United States Patent [19]
Chehab

[11] Patent Number: 5,489,507
[45] Date of Patent: Feb. 6, 1996

[54] DNA DETECTION BY COLOR COMPLEMENTATION

[75] Inventor: Farid F. Chehab, San Francisco, Calif.

[73] Assignee: Perkin-Elmer Corporation, Foster City, Calif.

[21] Appl. No.: 696,974

[22] Filed: May 1, 1991

Related U.S. Application Data

[63] Continuation of Ser. No. 277,751, Nov. 30, 1988, abandoned.

[51] Int. Cl.$^6$ ............................ C12Q 1/68; C12P 19/34
[52] U.S. Cl. ............................................ 435/6; 435/91.2
[58] Field of Search ............................ 435/6, 91, 803, 435/91.2; 436/26, 27, 28, 29

[56] References Cited

U.S. PATENT DOCUMENTS

| | | | |
|---|---|---|---|
| 3,892,530 | 7/1975 | Felix et al. | 436/90 |
| 4,495,293 | 1/1985 | Shaffar | 436/250 |
| 4,581,333 | 4/1986 | Kourilsky et al. | 435/6 |
| 4,683,195 | 7/1987 | Mullis et al. | 435/91 |
| 4,683,202 | 7/1987 | Mullis | 435/91 |

FOREIGN PATENT DOCUMENTS 0063879  11/1982  European Pat. Off. ................ 435/6

OTHER PUBLICATIONS

"Polymerase Chain Reaction–*Product Application Focus*", Christian Oste, *BioTechniques*, vol. 6, No. 2, 1988.
"Length mutations in human mitochondrial DNA: direct sequencing of enzymatically amplified DNA", Lisa A. Wrischnik, Russell G. Higuchi, Mark Stoneking, Henry A. Erlich, Norman Arnheim and Allan C. Wilson, *Nucleic Acids Research*, vol. 15, No. 2, 1987.
Yamane et al, *Nucleic Acids Research*, Symposium Series No. 20, pp. 91–92 (1988).
Landegren et al, Science, vol. 242, pp. 229–237 (1988).
Smith et al. (1985) The Synthesis of Oligonucleotides Containing an Aliphatic Amino Group at the $S^1$ Terminus Nuc. Acid. Res. 13(7)2399–2412.
Connolly B. (1985) Chemical Synthesis of Oligonucleotides Cont. a Freee Sulphydryl Group & Subsequent . . . Nu. Acid Res. 13 (12) 4483:4501.
Agrawal S (1986) Efficient Methods for Attaching Non–Radioactive Labels to The $S^1$ of Synth. Oligo . . . Nu. Acid Res 14(15) 6227–45.

*Primary Examiner*—W. Gary Jones
*Assistant Examiner*—Amy Atzel
*Attorney, Agent, or Firm*—Stephen C. Macevicz

[57] ABSTRACT

A method of detecting a target DNA in a sample is provided which includes simultaneously amplifying the target DNA and one or more internal standard DNAs, labeling the target DNA with a first color-producing or color-absorbing label, and labeling each of the one or more internal standard DNAs with a different second color-producing or color-absorbing label, the first and second color-producing and color-absorbing labels being selected so that upon illumination of the sample a first color signal is produced whenever the target DNA is present and a second color signal is produced whenever the target DNA is absent.

8 Claims, 1 Drawing Sheet

DNA DETECTION BY COLOR COMPLEMENTATION

This application is a continuation of Ser. No. 07/277,751 filed Nov. 30, 1988, now abandoned.

FIELD OF THE INVENTION

The invention relates generally to methods of detecting deoxyribonucleic acid (DNA) in diagnostic or forensic samples, and more particularly, to a method for indicating the presence or absence of a predetermined sequence of DNA in a sample by the generation of different colored signals.

BACKGROUND

Many disease states are associated with rearrangements, deletions, or additions of genetic material. Such alterations may be inherited, as in the case of genetic disorders, e.g. sickle cell disease, phenylketonuria, cystic fibrosis, and the like; or they may be acquired, as in the case of some cancers, e.g. chronic myelogenous leukemia, and some infectious diseases, e.g. Epstein-Barr virus infections. As the understanding of the molecular basis for such disease states has increased, a class of diagnostic techniques has been developed which are based on the direct detection of DNA sequences associated with the disease conditions, e.g. Caskey, *Science*, Vol. 236, pgs. 1223–1228 (1987); White et al, *Science*, Vol. 240, pgs. 1483–1488 (1988); and Landegren et al, *Science*, Vol. 242, pgs. 229–237 (1988). These techniques have also found application in forensic science for detecting the presence of polymorphic forms of genes, e.g. Landegren et al (cited above).

Generally, application of the above techniques depends on two factors: (1) the ability to acquire a sufficient amount of the target DNA for analysis, and (2) the means for generating a signal indicating the presence or absence of the target DNA. Applicability of some of these DNA-based diagnostic techniques is limited because they require relatively large amounts of DNA for analysis, e.g. restriction fragment length polymorphism (RFLP) analysis, Lindegren et al (cited above). In other cases, applicability is limited, or rendered more difficult, because components of a diagnostic sample must be separated for subsequent detection of the target DNA, e.g. by electrophoresis, chromatography, filtering, or the like. Recently, the former problem has been solved for many cases by DNA amplification techniques, such as polymerase chain reaction (PCR), e.g. Saiki et al, *Science*, Vol. 230, 1350–1354 (1985); Mullis et al, *Meth. Enzymol.*, Vol. 155, pgs. 335–350 (1987); and Mullis, U.S. Pat. No. 4,683,202; and more recently by the ligation amplification reaction (LAR), e.g. Skolnick and Wallace, *Genomics*, Vol. 2, pgs. 273–279 (1988). However, the latter problem (separation before detection), still complicates and increases the difficulty of implementing many DNA-based diagnostic assays, particularly when the separation step involves electrophoresis, e.g. Mullis (cited above).

The availability of a simple method for generating a signal which is amenable to automation and which indicates the presence or absence of a target DNA without the need of an electrophetic separation step would greatly facilitate the use of many DNA-based assays, especially in clinical and forensic settings.

SUMMARY OF THE INVENTION

The invention is directed to a method of detecting the presence or absence of one or more target DNA sequences by color complementation of a plurality of color-producing and/or color-absorbing labels, at least one being associated with each target DNA and at least one being associated with each internal standard DNA present in a sample. The invention also includes kits for carrying out the method of the invention.

As used herein, "target DNA" means the nucleic acid sequence whose presence or absence is to be determined. The sequence of the target DNA may be associated with a translocation, an inversion, single- or multiple-base deletions or substitutions, viral integration, polymorphisms, or the like. As used herein, "internal standard DNA" means a nucleic acid which will be present in a sample whether or not the target DNA is present and which can be labeled and detected independently of the target DNA. For example, the internal standard DNA may correspond to a known sequence of DNA, e.g. a gene, on a chromosome different from that on which the target DNA is located. As used herein, "sample" refers to the collection of DNAs, usually derived from a biological source, which may contain a target DNA. A sample may contain other materials, such as cellular debris, solvents, buffers, stabilizing reagents, or the like. And a sample may have undergone one or more processing steps before the application of the invention. For example, a sample may consist of DNA extracted from a tissue sample, DNA reverse transcribed from RNA extracted from a tissue sample, or the like. As used herein, "color complementation" means that the plurality of color-producing and/or color-absorbing labels in association generate a different color signal depending on whether a target DNA is present in a sample or not. Preferably, different colors under the invention are discernibly different to the human eye. However, in the context of instruments for carrying out the method of the invention, "different color" is meant to include light signals having wavelength characteristics distinguishable by standard photodetectors, whether or not they are distinguishable by the human eye.

An important feature of the invention is the simultaneous amplification in the sample of the one or more target DNAs, if present, and the one or more internal standard DNAs. Such amplification can be accomplished by a polymerase chain reaction or by a ligation amplification reaction, and the plurality of color-producing and color-absorbing labels are operationally associated with different pairs of primers (for PCR) or different pairs of adjacent oligonucleotides (for LAR) used to simultaneously amplify the target DNA(s) and the internal standard DNA(s).

DETAILED DESCRIPTION OF THE INVENTION

Figure 1:
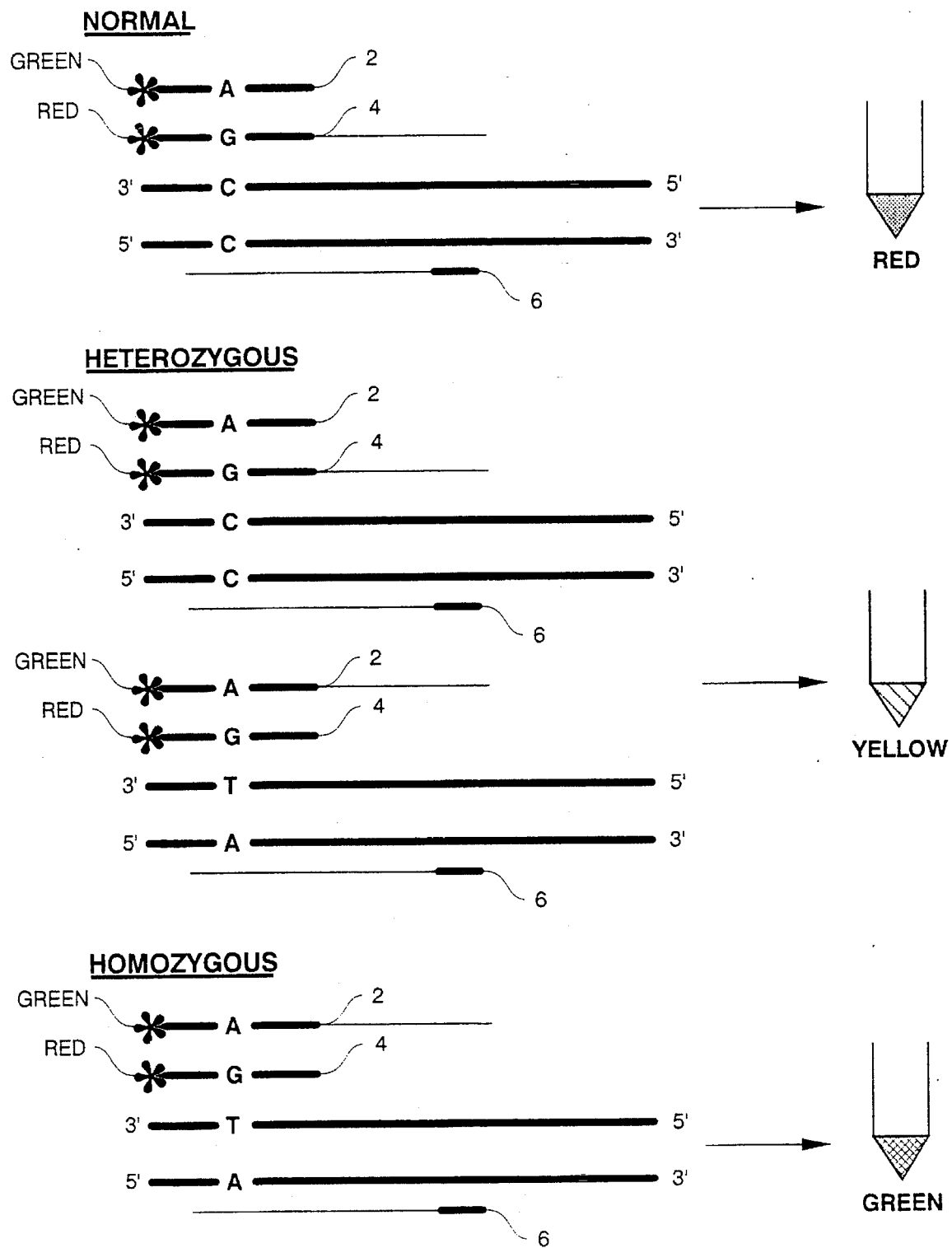
FIG. 1 diagrammatically illustrates one embodiment of the invention wherein an internal standard DNA is not necessarily amplified.

The invention is a method for detecting the presence or absence of one or more target DNAs. In one embodiment of the method comprises the steps of (i) simultaneously amplifying one or more target DNAs and one or more internal standard DNAs in a sample, (ii) providing one or more first labeling means capable of binding to the one or more targets DNA in the sample, respectively, (iii) providing one or more second labeling means capable of binding to one or more internal standard DNAs in the sample, respectively, (iv) combining the one or more first labeling means and the one or more second labeling means with the sample so that the one or more first labeling means binds to their one or more repective target DNAs to form one or more labeled target DNAs and the one or more second labeling means bind to their respective internal standard DNAs to form one or more labeled internal standard DNAs, respectively, (v) separating the unbound first labeling means from the sample, and (vi) illuminating the sample with an illumination beam having a predetermined wavelength characteristic such that a distinct color signal is produced whose character depends on which of the one or more target DNAs that have been amplified. Preferably, the steps of simultaneously amplifying, providing a first labeling means, providing one or more second labeling means, and combining are achieved by carrying out a polymerase chain reaction wherein the first labeling means comprises a pair of primers specific for the target DNA, at least one of the primers being labeled directly or indirectly with a first color-producing or color-absorbing label, and wherein the one or more second labeling means comprise separate pairs of primers, at least one member of each pair being labeled directly or indirectly with a different second color-producing or color-absorbing label. The term "primer" is used in the sense defined by Mullis U.S. Pat. No. 4,683,202, which is incorporated herein by reference for its disclosure of PCR. Generally, primers are oligonucleotides which act as synthesis initiation agents for a DNA polymerase. Primers are readily synthesized by standard techniques. Detailed procedures for the phosphite triester and hydrogen phosphonate methods of oligonucleotide synthesis are described in the following references, which are incorporated by reference: Caruthers et al, U.S. Pat. Nos. 4,458,066 and 4,500,707; Matteucci et al, *J. Amer. Chem. Soc.*, Vol. 103, pgs. 3185–3191 (1981); Caruthers et al, *Genetic Engineering*, Vol. 4, pgs. 1–17 (198 ); Jones, chapter 2, and Atkinson et al, chapter 3, in Gait, ed., *Oligonucleotide Synthesis: A Practical Approach* (IRL Press, Washington, D.C., 1984); Froehler et al, *Tetrahedron Letters*, Vol. 27, Pgs. 469–472 (1986); Garegg et al, *Tetrahedron Letters*, Vol. 27, pgs. 4051–4054 and 4055–4058 (1986); and Froehler et al, *Nucleic Acids Research*, Vol. 14, pgs. 5399–5407 (1986).

The steps of simultaneoulsly amplifying, providing one or more first labeling means, providing one or more second labeling means, and combining can also be carried out by a ligation amplification reaction wherein the one or more first labeling means comprise separate pairs of adjacent oligonucleotides specific for the target DNAs, and wherein the one or more second labeling means comprise separate pairs of adjacent oligonucleotides specific for the internal standard DNAs. Accordingly, the reference Skolnick and Wallace (cited above) is incorporated by reference.

Another embodiment of the method does not require that an internal standard DNA necessarily be amplified. In this embodiment, illustrated in FIG. 1, the zygosity of a particular base substitution is determined by color complementation. (In this case, the normal allelic form can be viewed as an internal standard DNA; thus, in a sample from an individual homozygous in the abnormal allele there is no amplification). A labeled primer, e.g. 2 and 4 of FIG. 1, is prepared for each allelic form, and an unlabeled primer, 6, is prepared to drive the PCR. If the sample contains only DNA corresponding to the normal allele (A) a first color is generated, e.g. red. If the sample contains a copy of both the normal allele and the abnormal allele (B), then a second color forms, e.g. yellow. If the sample contains only DNA corresponding to the abnormal allele (C), then a third color forms, e.g. green.

Color-producing labels and color-absorbing labels can be attached to primers in a variety of ways either directly or indirectly. Matthews et al, *Anal. Biochem.*, Vol 169, pgs. 1–25 (1988) provide a comprehensive list of both direct and indirect labeling means for nucleic acids. Accordingly, this reference is incorporated by reference.

Labels can be directly attached to primers via a 5' amino or thiol linking group, e.g. Connolly et al, *Nucleic Acids Research*, Vol. 13, pgs. 4485–4502 (1985); and Fung et al, U.S. Pat. No. 4,757,141. Accordingly, these references are incorporated by reference. Many commercially available dyes with amino- or thiol-reactive moieties can be used as color-producing and/or color-absorbing labels. For example, the following dyes suitable for use with the invention are available from Molecular Probes, Inc. (Eugene, Oreg.): (i) thiol-reactive: 5-iodoacetamindofluorescein, fluorescein-5-maleimide, tetramethylrhodamine-5(and-6)iodoacetamide, rhodamine X iodoacetamide, and the like, and (ii) amino-reactive: Fluorescein-5(and6)isothiocyanate, Texas Red, rhodamine X isothiocyanate, fluorescein-5 (or-6)succinimidylcarboxylates, 7-amino-4-methylcoumarin-3-acetic acid, 5- and/or 6-succinimidylcarboxylates of rhodamine dyes, and the like, the latter dyes being disclosed in U.S. patent application Ser. No. 07/138,287 filed 24 Dec. 1987, which is incorporated herein by reference.

Color-producing and/or color-absorbing labels can also be attached to primers indirectly via antibodies or via biotin and avidin or streptavidin. Means for synthesizing biotinylated primers is well known in the art, e.g. Chollet et al, *Nucleic Acids Research*, Vol. 13, pgs. 1529–1541 (1985); and Agrawal et al, *Nucleic Acids Research*, Vol. 14, pgs. 6227–6245 (1986). Accordingly, these references are incorporated by reference. Biotinylating reagents are also commercially available, e.g. Molecular Probes, Inc. (Eugene, Oreg.).

One or more different internal standard DNAs can be amplified with primers having the same label in order to vary the relative concentrations of the color-producing or color-absorbing labels at the time of readout. For example, if one of the color-producing labels is a fluorescent dye with low fluorescent efficiency and a given degree of brightness is required for color complementation, a number of internal standard DNAs can be labeled with the same "weak" fluorescent label to increase the labels relative concentration, and hence, its relative brightness.

Preferably, in automated embodiments of the invention the first and second color-producing or color-absorbing means comprise pairs of PCR primers wherein the 5' nucleotide of one primer of the pair is covalently attached to biotin and wherein the 5' nucleotide of the other primer is directly labeled with a color-producing or color-absorbing label. Preferably, color-producing labels are fluorescent labels, such as fluorescein, Texas Red, tetramehylrhodamine, dichlorodimethoxyfluoroscein, or the like. In some cases, fluorescent labels can also act as color-absorbing labels. Preferably, color-absorbing labels are used with a first labeling means and are organic indicator molecules which can be linked to an amino- or thiol-derivatized primer and whose absorption spectrum substantially overlaps both the emission spectrum of the illumination beam and the emission spectrum of a fluorescent label used in conjunction with a second labeling means. That is, preferably, the color-absorbing label is associated with the target DNA and the fluorescent label is associated with an internal standard DNA. Color-absorbing labes suitable for use with the invention can be selected from those disclosed by Bishop, ed., *Indicators*, (Pergamon Press, Oxford, 1972). If a target DNA is present and amplified the measured absorption will be high and fluorescence will be low. The reverse holds if the target DNA is not present. The presence of the target DNA is determined by the ratio of absorption to fluorescence intensity.

Most preferably, both the first and second color-producing or color-absorbing labels are fluorescent labels. Preferably, a rhodamine dye (red), such as Texas Red, rhodamine X, or the like, is used with a fluorescein dye (green), such as fluorecein, dichlorodimethoxyfluorescein, or the like, to give a yellow signal if a target DNA is present and a red or green signal if it is not. Suitable fluorescein dyes are disclosed by Khanna et al, in U.S. Pat. Nos. 4,318,846; 4,439,356; and 4,481,136, which patents are incorporated by reference. When the above pairs of fluorescent dyes are used, they can be illuminated by a standard UV lamp or by an argon ion laser, e.g. operating at 488 and 512 nm.

The target and internal standard DNAs can be selected such that the amplification products can either be the same of different in size, since color detection is independent of DNA size, unlike conventional amplification/detection schemes which require electrophoretic separation of the amplification products.

As mentioned above, for automated embodiments it is preferred that the first and second labeling means comprise pairs of primers, one with biotin attached to its 5' end and the other with a color-producing or color-absorbing label attached to its 5' end. In such an embodiment, after amplification, the reaction mixture containing the amplified chains are exposed to an avidin or streptavidin derivatized substrate, e.g. magnetic microspheres (Advanced Magnetics, Inc., Cambridge, Mass.). This allows for rapid separation of the amplified chains from the rest of the reaction mixture which, for example, may contain a preponderance of labeled primers associated with the target DNA if the target DNA is not present in the sample (and consequently not amplified). Separation is readily carried out by filtration, or if magnetic microspheres are used, by magnetic separation. The labeled strands of the amplified DNA are separated from the biotinylated strands (and primers) by denaturation procedures, e.g. exposure to strong alkali solution (e.g. between 0.1 and 1.0 NaOH), or heat plus exposure to a solution of formamide and water. The biotinylated DNA is then removed with the substrate, and the remaining solution containing the labeled strands is illuminated by the illumination beam. Automation of the invention is readily carried out by use of a general purpose laboratory robot, such as that disclosed by Wilson et al, *BioTechniques*, Vol. 6, pgs. 776 (1988).

The following examples serve to illustrate the present invention. The concentrations of reagents, temperatures, and the values of other variable parameters are only to exemplify the invention and are not to be considered limitations thereof.

EXAMPLES

The oligonucleotides of Table II were synthesized on a 380B Applied Biosystems, Inc. (Foster City, Calif.) DNA synthesizer as 1 umole scale, deprotected overnight at 55° C. and dried in vacuo. The product was resuspended in 450 ul sterile distilled water. 15 ul were conjugated onvernight at pH 9.0 to either a rhodamine, coumarin, or fluorescein dye in a 27 ul reaction for 3 hours. The dye-labeled oligonucleotide was purified by gel filtration chromatography and high pressure liquid chromatography.

EXAMPLE I. Detection of a Large Deletion: Hydrops Fetalis

A 136 bp target alpha-globin and a 110 bp beta-globin internal standard DNA segments from a normal subject and an individual with deletion type hydrops fetalis were co-amplified by PCR. The 100 ul amplification reactions consisted of 1 ug genomic DNA from either subject, 30 picomoles each of target DNA primers 1 and 2, and internal standard DNA primers A and B (Table II), 50 mM KCl, 10 mM Tris (pH 8.1), 1,5 mM MgCl$_2$ and 100 uM dATP, dGTP, dCTP, and TTP. The reaction mixture was heated for 5 minutes at 95° C., cooled on ice and 1 ul (5 units/ul) of Thermus aquaticus DNA polymerase added. The reaction was layered with 35 ul mineral oil to prevent evaporation and incubated sequentially at 95° C. for 30 sec., 55° C. for 30 sec., and 68° C. for 30 sec. This heating and cooling cycle was repeated 30 times befor the reactions were stored at 4° C. To demonstrate the feasibility of the invention by conventional methods, a 15 ul aliquot from each amplification reaction was loaded on an 8% polyacrylamide gel and run a 30 mA for 45 min. The bands on the gel were visualized without any staining by UV irradiation. The remainder of the PCR reaction mixture was diluted to 2 ml with 10 mM Tris (pH 8.0) and loaded on a Centricon-100 spin dialysis column (AMICON) and centrifuged for 10 min. at 5000 rpm in a fixed angle rotor. The retentate was pipetted out and the color of the PCR products were visualized by UV. Typically, in the application of the invention no gel electrophoresis would be required after the completion of the amplification

EXAMPLE II. Detection of a Translocation: the 14.18 Breakpoint in Telicular Lymphomas A PCR reaction was set up as described above with genomic DNA from a normal individual and from a cell line FL218 which carries the 14.18 translocation. Target DNA primers 3 and 4 and internal standard DNA primers C and D were used. The PCR reaction cycle temperatures were the same as in Example I. The color of the PCR reaction mixtures was visualized by exposing them to UV light.

Further examples of detecting target DNAs and internal standard DNAs were carried out as indicated in Table I. The PCR reaction conditions were identical to those of Example I.

TABLE I

Further Example of DNA Detection by Color Complementation

| CONDITION | TARGET PRIMERS | INT. STD. PRIMERS |
|---|---|---|
| Cytomegalovirus | 5 and 6 | A and B |
| 4 basepair deletion at codons 41–42 in beta-thalassemia | 7, 8, and 9 | |
| G->A substitution at position 110 of the intervening sequence 1 in beta-thalassemia | 9, 10, and 11* | |

*It was found that detection occurred most favorably in this example when the PCR started with primers 10, 11, and 9 at the concentrations of 40 picomolar, 10 picomolar, and 40 picomolar, respectively.

TABLE II

Target DNA Primers and Internal Standard DNA Primers

| NUMBER | SEQUENCE |
| --- | --- |
| 1 | 5'(dye)TACTGTAGATACCCGTGTACAA |
| 2 | 5'(dye)ATCATGATGGAAACATAGTAAT |
| 3 | 5'(dye)CCTTTAGAGAGTTGCTTTACGT |
| 4 | 5'(dye)ACCTGAGGAGACGGTGACCAGG |
| 5 | 5'(dye)TTCGTGTGTCCCCGGGGACCC |
| 6 | 5'(dye)GCACGGCGAAAAGAAGACGCG |
| 7 | 5'(dye)CAGAGGTTCTTTGAGTCCT |
| 8 | 5'(dye)CTGCCTATTAGTCTATTTT |
| 9 | 5'GCCATCACTAAAGGCACCG |
| 10 | 5'(dye)CTGCCTATTGGTCTATTTT |
| 11 | 5'(dye)CTGCCTATTAGTCTATTTT |
| A | 5'(dye)CAGAGGTTCTTTGAGTCCT |
| B | 5'(dye)GCCATCACTAAAGGCACCG |
| C | 5'(dye)TGGACACCCCTACCATCATACTGTAGATACCCGTGTACAA |
| D | 5'(dye)ATCATGATGGAAACATAGTAATAATCAGTGAGACTGTGGA |

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

I claim:

1. A method of determining the zygosity of an individual at a predetermined genetic locus having one or more allelic forms of DNA, the method comprising the steps of:

providing a labelling means for each of the one or more allelic forms of DNA, such that each labelling means comprises a pair of oligonucleotides, each oligonucleotide of the pair being capable of forming perfectly matched duplexes at different and nonoverlapping regions of the same allelic form of DNA, and such that each labelling means is capable of producing a light signal different from every other labelling means;

combining the labelling means with the sample;

simultaneously amplifying the allelic forms of DNA forming perfectly matched duplexes with the pairs of oligonucleotides of their respective labelling means;

separating from the amplified allelic forms of DNA, any labelling means having an oligonucleotide incapable of forming a perfectly matched duplex with any of the allelic forms of DNA; and illuminating the amplified allelic forms of DNA with an illumination beam such that a distinct light signal is produced by color complementation of the light signals generated by the labelling means associated with the amplified allelic forms of DNA.

2. The method of claim 1 wherein said steps of providing, combining, and simultaneously amplifying include the steps of:

providing pairs of primers for said allelic forms of DNA, at least one primer of each pair being labeled with a color-producing or color-absorbing label;

simultaneously amplifying by polymerase chain reaction said allelic forms of DNA whose primers both form perfectly matched duplexes therewith.

3. The method of claim 2 wherein said step of providing pairs of primers for said allelic forms of DNA includes providing one primer of each pair labeled with said color-producing or color-absorbing label and the other primer of each pair biotinylated.

4. The method of claim 3 wherein said step of separating includes:

providing a solid phase support derivatized with avidin or streptavidin;

reacting said amplified allelic forms of DNA with the solid phase support so that said biotinylated primers bind to the avidin or streptavidin of the solid phase support;

washing the solid phase support to remove said primers incapable of forming perfectly matched duplexes with said allelic forms of DNA and labeled with a color-producing or color-absorbing label;

denaturing said amplified allelic forms of DNA bound to the solid phase support to form labeled single stranded allelic forms of DNA; and separating the labeled single stranded allelic forms of DNA from the solid phase support.

5. The method of claim 4 wherein said color-producing or color-absorbing label for at least one of said allelic forms of DNA is a fluorescein dye.

6. The method of claim 5 wherein said color-producing or color-absorbing label for at least one of said allelic forms of DNA is selected from the group consisting of a rhodamine dye and coumarin.

7. The method of claim 6 wherein said solid phase support consists of magnetic microspheres.

8. The method of claim 7 wherein said fluorescein dye is fluorescein and said rhodamine dye is rhodamine X.

* * * * *